US008063189B2

(12) United States Patent
Arunakumari et al.

(10) Patent No.: US 8,063,189 B2
(45) Date of Patent: Nov. 22, 2011

(54) PROTEIN PURIFICATION BY CITRATE PRECIPITATION

(75) Inventors: Alahari Arunakumari, Pennington, NJ (US); Gisela M. Ferreira, Gaithersburg, MD (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/759,016

(22) Filed: Apr. 13, 2010

(65) Prior Publication Data

US 2010/0261886 A1 Oct. 14, 2010

Related U.S. Application Data

(60) Provisional application No. 61/168,920, filed on Apr. 13, 2009.

(51) Int. Cl.
*C07K 1/30* (2006.01)
*C07K 1/36* (2006.01)

(52) U.S. Cl. ..................... 530/390.5; 530/419

(58) Field of Classification Search .................. None
See application file for complete search history.

(56) References Cited

U.S. PATENT DOCUMENTS

| 4,321,192 | A | * | 3/1982 | Jain ............................... 530/420 |
| 4,835,257 | A | * | 5/1989 | Friedrich-Fiechtl et al. ............................ 424/177.1 |
| 4,977,246 | A | * | 12/1990 | Lee et al. ........................ 530/383 |
| 5,371,198 | A | * | 12/1994 | Joergensen et al. ............. 530/412 |
| 7,041,798 | B1 | * | 5/2006 | Kothe et al. ..................... 530/364 |
| 7,879,332 | B2 | * | 2/2011 | Zurlo et al. ................. 424/177.1 |
| 2005/0196393 | A1 | | 9/2005 | Shanbrom |
| 2006/0223988 | A1 | | 10/2006 | Maurer |
| 2007/0049734 | A1 | * | 3/2007 | Zurlo et al. ................. 530/387.1 |

FOREIGN PATENT DOCUMENTS

WO    WO 2008/100578    8/2008

OTHER PUBLICATIONS

Ahamed, T. et al., "Selection of pH-related parameters in ion-exchange chromatography using pH-gradient operations", Journal of Chromatography A., vol. 1194, No. 1, pp. 22-29 (2007).

Arunakumari, A. et al., "Alternatives to Protein A: Improved Downstream Process design for Human Monoclonal Antibody Production", Biopharm International, 9 pages, Feb. 2, 2007.
Foster, P.R. et al., "The Kinetics of protein salting-out : precipitation of yeast enzymes by ammonium sulfate", Biotechnology and Bioengineering, vol. 18, No. 4, pp. 545-580 (2004).
Gagnon, P., "Purification tools for Monoclonal Antibodies", Validated Biosystems, Tucson AZ (ISBN: 0965351599) (1996).
Gagnon, P., "Use of Hydrophobic Interaction Chromatography with a Non-Salt Buffer system for Improving process Economics in Purification of Monoclonal Antibodies", Waterside Conference on Monoclonal and Recombinant Antibodies. Miami FL, Tosoh. (2000) Abstract.
Matheus, S., et al., "Liquid high concentration IgG1 antibody formulations by precipitation", J. of Pharmaceutical Science (Epub—2008).
Wang, J. et al., "Optimizing the primary recovery step in nonaffinity purification schemes for HuMAbs", BioPharm International (2008).
Zellner, et al., "Quantitative validation of different protein precipitation methods in proteome analysis of blood platelets", Electrophoresis, vol. 26, No. 12, pp. 2481-2489 (2005).
Bizhanov, G. et al., "A novel method, based on lithium sulfate precipitation for purification of chicken egg yolk immunoglobulin Y, applied to immunospecific antibodies against Sendai virus", Scandinavian Journal of Lab Animal Science, vol. 31, No. 3, pp. 121-130 (2004).
Moscariello, J., "Comparison of Potential Monoclonal Antibody Purification Processes with Two Chromatography Steps". BioProcess International Conference, Anaheim, CA. (2008).
Shields, C., "Advances in Single Use Capture Chromatography". BioProcess International Conference, Anaheim, CA. (2008).
Vilmorin, P., "Scale-up evaluation of selective antibody precipitation and continuous recovery with a disc-stack centrifuge". BioProcess International Conference, Anaheim, CA. (2008).

* cited by examiner

*Primary Examiner* — David A. Saunders
(74) *Attorney, Agent, or Firm* — Z. Angela Guo (57) ABSTRACT

The invention provides methods for isolating proteins in purified form from mixtures by precipitation with citrate. The methods are advantageous in that they effectively separate a protein from lower molecular weight contaminants, including fragments or portions of the protein. Such methods are particularly useful for purifying antibodies from mixtures containing antibody proteolytic fragments and unpaired chains.

13 Claims, 4 Drawing Sheets

PROTEIN PURIFICATION BY CITRATE PRECIPITATION

CROSS-REFERENCE TO RELATED APPLICATIONS

This application claims the benefit under 35 U.S.C. §119(e) of U.S. Provisional Application No. 61/168920, filed Apr. 13, 2009, the disclosure of which is incorporated herein by reference.

BACKGROUND OF THE INVENTION

The large-scale, economic purification of proteins such as antibodies is an increasingly important problem for the biopharmaceutical industry. Therapeutic proteins are typically produced using prokaryotic or eukaryotic cell lines that are engineered to express the protein of interest from a recombinant plasmid containing the gene encoding the protein. Separation of the desired protein from the mixture of components fed to the cells and cellular by-products to an adequate purity, e.g., sufficient for use as a human therapeutic, poses a formidable challenge to biologics manufacturers for several reasons.

In the case of therapeutic antibodies, the current methods of purification involve the processing of large volumes of antibody-containing culture medium or cell lysates, from which the antibody is ultimately separated by chromatography. The rate limiting step in this method is the processing time associated with the large volume of antibody-containing starting material. One solution to this problem is to reduce the volume of the starting material by precipitating the antibody and resuspending in a smaller volume prior to performing the chromatography step(s). In addition, this precipitation step also partially purifies the protein of interest from other contaminants in the cell culture harvest. However, prior traditional protein precipitation methods have limitations for large scale production of therapeutics. For example, the common protein precipitant, ammonium sulphate, is corrosive and prone to releasing gaseous ammonia. Recent efforts at large scale antibody precipitation involved use of polyethylene glycol (PEG) as a precipitant (see US 2008/0214795, incorporated herein by reference in its entirety). However, this process can be challenging at large scale and the antibody precipitate so formed is difficult to resuspend in aqueous buffers.

Accordingly there is a need in the art for alternative antibody precipitation methods that can be used to expedite the large-scale processing of proteins, in particular antibodies.

BRIEF SUMMARY OF THE INVENTION

The present invention is based on the discovery that proteins, particularly antibodies, can be efficiently purified (i.e., separated from a mixture comprising the protein and at least one contaminant) by precipitation with citrate. The methods of the invention are advantageous in that the protein precipitate formed by the citrate can be readily resolubilized in a small volume of buffer. Importantly, the methods also effectively separate the protein from lower molecular weight (e.g., less than about 50 kDa) contaminants, including derivatives (e.g., fragments or portions) of the protein. Thus, when used to purify an antibody, for example, the method isolates the antibody from small contaminants, such as antibody proteolytic fragments and unpaired chains (e.g., light chains).

Accordingly, in one aspect, the invention provides a method of isolating a protein (including, but not limited to, antibodies) from a mixture comprising one or more contaminants (including, but not limited to, host cell contaminants). The method generally comprises adding citrate to the mixture to precipitate the protein and thereby separate it from the mixture. Any suitable citrate salt can be used including, without limitation, disodium citrate (also known as sodium citrate). In a particular embodiment, the citrate is added to the mixture to a final citrate concentration of at least about 0.5 M, for example, about 0.6, 0.7, 0.8, 0.9, or 1.0 M, e.g., between about 0.5 and 1.0 M. In an embodiment, the final citrate concentration is between about 0.5 and about 1.0 M. In another particular embodiment, the citrate is added with one or more additional compounds which reduce the amount of citrate required to form the antibody precipitate. Such compounds include, for example, ammonium sulphate. The protein precipitate can then be isolated from the mixture using a variety of art recognized means including, without limitation, centrifugation, filtration or tangential flow filtration.

In another particular embodiment, the method further comprises reducing the ionic concentration of the precipitate, thereby allowing the protein to be captured by ion exchange, hydrophobicity and mixed mode affinity resins. This can be achieved, by for example, using a wash buffer to reduce the ionic concentration of the antibody precipitate. Suitable wash buffers include, for example, aqueous buffers comprising a polyether such as polyethylene glycol (PEG). Preferably the PEG has a molecular weight between about 0.25 to 50 kD (e.g., about 3 to 10 kD) and has a concentration (in solution) of up to about 35% weight/volume (w/v) (e.g., about 5%, 10% or 15% w/v). In a particular embodiment, the volume of the wash buffer is between about 1 to 10 times the volume of the antibody precipitate, such as about 2, 3, 4, 5, 6, 7, 8 or 9 times the volume of the antibody precipitate.

The methods of the invention typically result in isolation (i.e., within the precipitate), of at least about 50% intact protein (e.g., antibody), more preferably about 60%, 70%, 80%, 90% or 95% intact protein. In particular embodiment, the precipitate contains less than about 2 µg/mL of protein contaminants, for example, about 1, 0.1, 0.01, or 0.001 µg/mL of protein contaminants.

Following addition of citrate to the mixture and isolation of the resultant precipitate, the precipitate can be resuspended in a suitable buffer to form a protein solution. In a particular embodiment, the volume of the protein solution is about four fold less than the volume of the initial mixture. In another particular embodiment, the protein solution has a conductivity of less than about 20 mS/cm. In another particular embodiment, the recovery of the protein is at least about 80%, for example, about 85%, 90%, 95% or 98%. In another particular embodiment, the protein solution is subjected to ion exchange chromatography, affinity, mimetic or mixed mode chromatography to further purify the protein.

Thus, in one embodiment there is provided a method of isolating a protein from a mixture comprising the protein and one or more contaminants comprising: (a) adding citrate to the mixture to form a protein precipitate (also referred to herein as "a precipitate of the protein"); (b) separating the protein precipitate from the mixture; and (c) reducing the ionic concentration of the protein precipitate by contacting the protein precipitate with a wash buffer, thereby isolating the protein from the mixture. As a further step of the invention, the protein precipitate may be dissolved in a solvent to form a protein solution (also referred to herein as "a solution of the protein") and subjected to ion exchange chromatography, hydrophobic interaction chromatography, affinity chromatography, mimetic chromatography, or mixed mode chromatography, to further purify the protein.

In another embodiment, this invention provides method of obtaining a protein in purified form from a mixture comprising the protein and one or more contaminants, comprising: (a) adding citrate to the mixture to form a precipitate of the protein; and (b) separating the precipitate of the protein from the mixture. The method may comprise a further step of reducing the ionic concentration of the protein by contacting the precipitate of the protein with a wash buffer. The method may also include the further steps of dissolving the precipitate of the protein in a solvent to form a solution of the protein and subjecting the solution to ion exchange chromatography, hydrophobic interaction chromatography, affinity chromatography, mimetic chromatography, or mixed mode chromatography, to further purify the protein, with or without employing the ionic concentration reduction step.

The invention can be used to purify any type of protein from a mixture, such as an antibody, in particular a monoclonal antibody (e.g., a human, humanized or chimeric monoclonal antibody) or a fragment thereof, from a cell culture supernatant (e.g., a mammalian, bacterial or fungal cell culture cell culture supernatant) or transgenic plant or animal derived protein mixtures or extracts. Preferably, the protein precipitate comprises less than 2 µg/mg of contaminant protein.

DETAILED DESCRIPTION OF THE INVENTION

Definitions

As used herein, a "mixture" comprises a protein of interest (for which purification is desired) and one or more contaminant, i.e., impurities. In one embodiment the mixture is produced from a host cell or organism that expresses the protein of interest (either naturally or recombinantly). Such mixtures include, for example, harvested cell culture fluid, cell culture supernatant and conditioned cell culture supernatant.

As used herein, the terms "separation", "purification" and "isolation" are used interchangeably, and refer to the selective removal of a protein (e.g. antibody) from a mixture. The invention achieves this by precipitation of the protein using citrate. Following precipitation, the protein precipitate can be removed from the mixture using any means compatible with the present invention, including common industrial methods such as centrifugation or filtration. This separation results in the recovery of a protein precipitate which is essentially free of soluble contaminants (e.g. small molecular weight contaminants, including, e.g., antibody proteolytic fragments or unpaired light chains).

As used herein, the term "precipitate" refers to an insoluble substance comprising a protein of interest (e.g. antibody) formed in a solution due to the addition of a compound (e.g., citrate) to the solution.

As used herein the term "contaminant" is used in its broadest sense to cover any undesired component or compound within a mixture. Such components include, for example, contaminating proteins present in cell culture media for mammalian, bacterial and fungal culture systems, including the host's cellular proteins, serum, blood, plasma, milk and their derivatives, and eggs (e.g., chicken). Such contaminant proteins include, without limitation, those naturally or recombinantly produced by the host cell, as well as proteins related to or derived from the protein of interest (e.g., proteolytic fragments) and other process related contaminants.

As used herein the term "citrate" refers to any citrate salt capable of precipitating a protein (e.g., an antibody) when added to a mixture or solution.

As used herein the term "recovery" or "recovered from the mixture refers to the total amount of protein (e.g., antibody) that can be resolubilized from the precipitate compared to the total amount of protein present in the starting mixture. For example, if a mixture contained 1 g of antibody and, after citrate precipitation of antibody from the mixture, 0.8 g of antibody was resolubilized from the resultant antibody precipitate, this would represent an 80% recovery of antibody.

As used herein the term "reducing the ionic concentration" refers to the removal of ionic species such that the electrical conductivity is reduced.

As used herein the term "wash buffer" refers to a solution used to remove one or more contaminants from a protein precipitate without resolubilizing the protein. In a preferred embodiment the wash buffer reduces the ionic concentration of the precipitate to facilitate subsequent ion exchange chromatography. The term "washing", and grammatical variations thereof, is used to describe contacting an appropriate wash buffer with an antibody precipitate or the chromatography resin.

As used herein, the term "conductivity" refers to the ability of an aqueous solution to conduct an electric current between two electrodes at a particular temperature. A current flows by ion transport in solution. Therefore, with an increasing concentration of ions present in the aqueous solution, the solution will have a higher conductivity. The unit of measurement for conductivity is milliSiemens per centimeter (mS/cm), and can be measured using a standard conductivity meter. The conductivity of a solution can be altered by changing the concentration of ions therein. For example, the concentration of a buffering agent and/or concentration of a salt (e.g. NaCitrate, NaCl or KCl) in the solution may be altered in order to achieve the desired conductivity or may be reduced by dilution with water.

The term "antibody" is used in the broadest sense to cover monoclonal antibodies (including full length monoclonal antibodies), polyclonal antibodies, multispecific antibodies (e.g., bispecific antibodies), antibody fragments, immunoadhesins and antibody-immunoadhesin chimeras.

An "antibody fragment" includes at least a portion of a full length antibody and typically an antigen binding or variable region thereof. Examples of antibody fragments include Fab, Fab', F(ab')$_2$, and Fv fragments; single-chain antibody molecules; diabodies; linear antibodies; and multispecific antibodies formed from engineered antibody fragments.

The term "monoclonal antibody" is used in the conventional sense to refer to an antibody obtained from a population of substantially homogeneous antibodies such that the individual antibodies comprising the population are identical except for possible naturally occurring mutations that may be present in minor amounts. Monoclonal antibodies are highly specific, being directed against a single antigenic site. This is in contrast with polyclonal antibody preparations which typically include varied antibodies directed against different determinants (epitopes) of an antigen, whereas monoclonal antibodies are directed against a single determinant on the antigen. The term "monoclonal", in describing antibodies, indicates the character of the antibody as being obtained from a substantially homogeneous population of antibodies, and is not to be construed as requiring production of the antibody by any particular method. For example, monoclonal antibodies used in the present invention can be produced using conventional hybridoma technology first described by Kohler et al., Nature 256:495 (1975), or they can be made using recombinant DNA methods (see, e.g., U.S. Pat. No. 4,816,567). Monoclonal antibodies can also be isolated from phage antibody libraries, e.g., using the techniques described in Clackson et al., Nature 352:624-628 (1991); Marks et al., J. Mol. Biol. 222:581-597 (1991); and U.S. Pat. Nos. 5,223,409; 5,403,484; 5,571,698; 5,427,908; 5,580,717; 5,969,108; 6,172,197; 5,885,793; 6,521,404; 6,544,731; 6,555,313; 6,582,915; and 6,593,081).

Monoclonal antibodies include "chimeric" and "humanized" antibodies. In a "chimeric antibody" a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). "Humanized" forms of non-human (e.g., murine) antibodies are chimeric antibodies which contain minimal sequence derived from non-human immunoglobulin. For the most part, humanized antibodies are human immunoglobulins (recipient antibody) in which the hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

Chimeric or humanized antibodies can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., Cabilly et al., U.S. Pat. No. 4,816,567). To create a humanized antibody, the murine CDR regions can be inserted into a human framework using methods known in the art (see e.g., Winter, U.S. Pat. No. 5,225,539 and Queen et al., U.S. Pat. Nos. 5,530,101; 5,585,089; 5,693,762 and 6,180,370).

The monoclonal antibodies also include "human" antibodies, which can be isolated from various sources such as the blood of a human patient or recombinantly prepared using transgenic animals. Examples of such transgenic animals include KM-Mouse® (Medarex, Inc., a subsidiary of Bristol-Myers Squibb Co.) which has a human heavy chain transgene and a human light chain transchromosome (see WO 2002/43478), Xenomouse® (Abgenix, Inc., Fremont Calif. (a subsidiary of Amgen, Inc.); as described in, e.g., Kucherlapati et al., U.S. Pat. Nos. 5,939,598; 6,075,181; 6,114,598; 6,150,584 and 6,162,963), and HuMAb-Mouse® (Medarex, Inc.; described in, e.g., Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci.* USA 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845-851, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807; and WO 92/03918, WO 93/12227, WO 94/25585, WO 97/13852, WO 98/24884 WO 99/45962, and WO 01/14424). Human monoclonal antibodies can also be prepared using SCID mice into which human immune cells have been reconstituted such that a human antibody response can be generated upon immunization. Such mice are described in, for example, U.S. Pat. Nos. 5,476,996 and 5,698,767.

As used herein, the term "tangential flow filtration" refers to a filtration process in which the sample mixture circulates across the top of a membrane, while applied pressure causes certain solutes and small molecules to pass through the membrane.

As used herein the term "chromatography" refers to the process by which a solute of interest, e.g., a protein of interest, in a mixture is separated from other solutes in the mixture by percolation of the mixture through an adsorbent, which adsorbs or retains a solute more or less strongly due to properties of the solute, such as pI, hydrophobicity, size and structure, under particular buffering conditions of the process.

As used herein the term "hydrophobic charge induction chromatography" (or "HCIC") is a type of mixed mode chromatographic process in which the protein of interest in the mixture binds to a dual mode (i.e., there is one mode for binding and another mode for elution), ionizable ligand [see Boschetti et al., 2000, Genetic Engineering News 20(13)] through mild hydrophobic interactions in the absence of added salts (e.g. a lyotropic salts). A "hydrophobic charge induction chromatography resin" is a solid phase that contains a ligand which has the combined properties of thiophilic effect (i.e., utilizing the properties of thiophilic chromatography), hydrophobicity and an ionizable group for its separation capability. Thus, an HCIC resin used in a method of the invention contains a ligand that is ionizable and mildly hydrophobic at neutral (physiological) or slightly acidic pH, e.g., about pH 5 to 10, preferably about pH 6 to 9.5. At this pH range, the ligand is predominantly uncharged and binds a protein of interest via mild non-specific hydrophobic interaction. As pH is reduced, the ligand acquires charge and hydrophobic binding is disrupted by electrostatic charge repulsion towards the solute due to the pH shift. Examples of suitable ligands for use in HCIC include any ionizable aromatic or heterocyclic structure (e.g. those having a pyridine structure, such as 2-aminomethylpyridine, 3-aminomethylpyridine and 4-aminomethylpyridine, 2-mercaptopyridine, 4-mercaptopyridine or 4-mercaptoethylpyridine, mercapto-acids, mercaptoalcohols, imidazolyl based, mercaptomethylimidazole, 2-mercaptobenzimidazole, aminomethylbenzimidazole, histamine, mercaptobenzimidazole, diethylaminopropylamine, aminopropylmorpholine, aminopropylimidazole, aminocaproic acid, nitrohydroxybenzoic acid, nitrotyrosine/ethanolamine, dichlorosalicylic acid, dibromotyramine, chlorohydroxyphenylacetic acid, hydroxyphenylacetic acid, tyramine, thiophenol, glutathione, bisulphate, and dyes, including derivatives thereof; see Burton and Harding, Journal of Chromatography A 814: 81-81 (1998) and Boschetti, Journal of Biochemical and Biophysical Methods 49: 361-389 (2001), which are hereby incorporated by reference in their entireties), which has an aliphatic chain and at least one sulfur atom on the linker arm and/or ligand structure. An example of an HCIC resin includes MEP HYPERCEL (Pall Corporation; East Hills, N.Y.).

The terms "ion-exchange" or "ion-exchange chromatography" refer to a chromatographic process in which an ionizable solute of interest (e.g., a protein of interest in a mixture) interacts with an oppositely charged ligand linked (e.g., by covalent attachment) to a solid phase ion exchange material under appropriate conditions of pH and conductivity, such that the solute of interest interacts non-specifically with the charged compound more or less than the solute impurities or contaminants in the mixture. The contaminating solutes in the mixture can be washed from a column of the ion exchange material or are bound to or excluded from the resin, faster or slower than the solute of interest. "Ion-exchange chromatography" specifically includes cation exchange, anion exchange, and mixed mode chromatographies.

The phrase "ion exchange material" refers to a solid phase that is negatively charged (i.e. a cation exchange resin) or positively charged (i.e. an anion exchange resin). In one embodiment, the charge can be provided by attaching one or more charged ligands (or adsorbents) to the solid phase, e.g. by covalent linking Alternatively, or in addition, the charge can be an inherent property of the solid phase (e.g. as is the case for silica, which has an overall negative charge).

A "cation exchange resin" refers to a solid phase which is negatively charged, and which has free cations for exchange with cations in an aqueous solution passed over or through the solid phase. Any negatively charged ligand attached to the solid phase suitable to form the cation exchange resin can be used, e.g., a carboxylate, sulfonate and others as described below. Commercially available cation exchange resins include, but are not limited to, for example, those having a sulfonate based group (e.g., MonoS, MiniS, Source 15S and 30S, SP Sepharose Fast Flow™, SP Sepharose High Performance from GE Healthcare, Toyopearl SP-650S and SP-650M from Tosoh, Macro-Prep High S from BioRad, Ceramic HyperD S, Trisacryl M and LS SP and Spherodex LS SP from Pall Technologies,); a sulfoethyl based group (e.g., Fractogel SE, from EMD, Poros S-10 and S-20 from Applied Biosystems); a sulphopropyl based group (e.g., TSK Gel SP 5PW and SP-5PW-HR from Tosoh, Poros HS-20 and HS 50 from Applied Biosystems); a sulfoisobutyl based group (e.g., (Fractogel EMD $SO_3^-$ from EMD); a sulfoxyethyl based group (e.g., SE52, SE53 and Express-Ion S from Whatman), a carboxymethyl based group (e.g., CM Sepharose Fast Flow from GE Healthcare, Hydrocell CM from Biochrom Labs Inc., Macro-Prep CM from BioRad, Ceramic HyperD CM, Trisacryl M CM, Trisacryl LS CM, from Pall Technologies, Matrx Cellufine C500 and C200 from Millipore, CM52, CM32, CM23 and Express-Ion C from Whatman, Toyopearl CM-650S, CM-650M and CM-650C from Tosoh); sulfonic and carboxylic acid based groups (e.g. BAKERBOND Carboxy-Sulfon from J.T. Baker); a carboxylic acid based group (e.g., WP CBX from J.T Baker, DOWEX MAC-3 from Dow Liquid Separations, Amberlite Weak Cation Exchangers, DOWEX Weak Cation Exchanger, and Diaion Weak Cation Exchangers from Sigma-Aldrich and Fractogel EMD COO— from EMD); a sulfonic acid based group (e. g., Hydrocell SP from Biochrom Labs Inc., DOWEX Fine Mesh Strong Acid Cation Resin from Dow Liquid Separations, UNOsphere S, WP Sulfonic from J. T. Baker, Sartobind S membrane from Sartorius, Amberlite Strong Cation Exchangers, DOWEX Strong Cation and Diaion Strong Cation Exchanger from Sigma-Aldrich); and a orthophosphate based group (e.g., P11 from Whatman).

An "anion exchange resin" refers to a solid phase which is positively charged, thus having one or more positively charged ligands attached thereto. Any positively charged ligand attached to the solid phase suitable to form the anionic exchange resin can be used, such as quaternary amino groups Commercially available anion exchange resins include DEAE cellulose, Poros PI 20, PI 50, HQ 10, HQ 20, HQ 50, D 50 from Applied Biosystems, Sartobind Q from Sartorius, MonoQ, MiniQ, Source 15Q and 30Q, Q, DEAE and ANX Sepharose Fast Flow, Q Sepharose high Performance, QAE SEPHADEX™ and FAST Q SEPHAROSE™ (GE Healthcare),WP PEI, WP DEAM, WP QUAT from J.T. Baker, Hydrocell DEAE and Hydrocell QA from Biochrom Labs Inc., UNOsphere Q, Macro-Prep DEAE and Macro-Prep High Q from Biorad, Ceramic HyperD Q, ceramic HyperD DEAE, Trisacryl M and LS DEAE, Spherodex LS DEAE, QMA Spherosil LS, QMA Spherosil M and Mustang Q from Pall Technologies, DOWEX Fine Mesh Strong Base Type I and Type II Anion Resins and DOWEX MONOSPHER E 77, weak base anion from Dow Liquid Separations, Intercept Q membrane, Matrex Cellufine A200, A500, Q500, and Q800, from Millipore, Fractogel EMD TMAE, Fractogel EMD DEAE and Fractogel EMD DMAE from EMD, Amberlite weak strong anion exchangers type I and II, DOWEX weak and strong anion exchangers type I and II, Diaion weak and strong anion exchangers type I and II, Duolite from Sigma-Aldrich, TSK gel Q and DEAE 5PW and 5PW-HR, Toyopearl SuperQ-650S, 650M and 650C, QAE-550C and 650S, DEAE-650M and 650C from Tosoh, QA52, DE23, DE32, DE51, DE52, DE53, Express-Ion D and Express-Ion Q from Whatman.

A "mixed mode ion exchange resin" refers to a solid phase which is covalently modified with cationic, anionic, and/or hydrophobic moieties. Examples of mixed mode ion exchange resins include BAKERBOND ABX™ (J. T. Baker; Phillipsburg, N.J.), ceramic hydroxyapatite type I and II and fluoride hydroxyapatite (BioRad; Hercules, Calif.) and MEP and MBI HyperCel (Pall Corporation; East Hills, N.Y.).

Protein Mixtures

The methods of the invention can be applied to any protein-containing mixture. In one embodiment, the mixture is obtained from or produced by living cells that express, naturally or by genetic engineering, the protein to be purified. Methods of genetically engineering cells to produce proteins are well known in the art. See e.g. Ausabel et al., eds. (1990), Current Protocols in Molecular Biology (Wiley, New York) and U.S. Pat. Nos. 5,534,615 and 4,816,567, each of which are specifically incorporated herein by reference. Such methods include introducing nucleic acids that encode and allow expression of the protein into living host cells. These host cells can be bacterial cells, fungal cells, or, preferably, animal cells grown in culture. Bacterial host cells include, but are not limited to *Escherichia coli* cells. Examples of suitable *E. coli* strains include: HB101, DH5α, GM2929, JM109, KW251, NM538, NM539, and any *E. coli* strain that fails to cleave foreign DNA. Fungal host cells that can be used include, but are not limited to, *Saccharomyces cerevisiae, Pichia pastoris* and *Aspergillus* cells. A few examples of animal cell lines that can be used are CHO, VERO, DXB11, BHK, HeLa, Cos, MDCK, 293, 3T3, NS0 and WI138. New animal cell lines can be established using methods well know by those skilled in the art (e.g., by transformation, viral infection, and/or selection). In particular embodiments, the protein of interest (e.g., an antibody) is produced in a CHO cell (see, e.g., WO 94/11026). Various types of CHO cells are known in the art, e.g., CHO-K1, CHO-DG44, CHO-DXB11, CHO/dhfr⁻ and CHO-S.

Preparation of a mixture from cellular debris initially depends on the manner of expression of the protein. Some cell systems directly secrete the protein (e.g., an antibody) from the cell into the surrounding growth media, while other systems retain the antibody intracellularly. For proteins produced intracellularly, the cell can be disrupted using any of a variety of methods, such as mechanical shear, osmotic shock, and enzymatic treatment. The disruption releases the entire contents of the cell into the homogenate, and in addition produces subcellular fragments which can be removed by centrifugation or by filtration. A similar problem arises, although to a lesser extent, with directly secreted proteins due to the natural death of cells and release of intracellular host cell proteins during the course of the protein production run.

The method of the invention can employ any suitable methodology to remove cellular debris. If the protein is produced intracellularly, as a first step, the particulate debris, either host cells or lysed fragments, can be removed, for example, by a centrifugation or filtration step in order to prepare a mixture which is then subjected to purification according the methods described herein (i.e., from which a protein of interest is purified). If the protein is secreted into the medium, the recombinant host cells may be separated from the cell culture medium by, e.g., centrifugation, tangential flow filtration or depth filtration, in order to prepare a mixture from which a protein of interest is purified.

Protein Precipitation Using Citrate

According to the present invention, isolation of a protein of interest from contaminants within a mixture, particularly a cell culture medium, is achieved by precipitation with citrate. Any citrate salt may be used in the method of the invention including, without limitation, disodium citrate. Other citrate salts that can be used include potassium citrate and ammonium citrate. The citrate can be added to the mixture as a solid, a solution or a mixture of both. The precise concentration of citrate required to precipitate the protein can be determined empirically using the methods exemplified herein. The amount of citrate required to precipitate the protein can be reduced by the addition of co-precipitants. Compounds suitable for use as co-precipitants are well known in the art including, without limitation, ammonium sulphate. The protein precipitate can then be separated from the mixture by any art recognized means, such as centrifugation, filtration or tangential flow filtration.

Washing the Protein Precipitate

The protein precipitate can be washed to further remove contaminants and/or to reduce the ionic concentration of the precipitate. Any suitable wash buffer that is capable of removing contaminants and/or reducing the ionic concentration of the precipitate, without solubiling the precipitate, can be used. Aqueous polyether solutions are particularly advantageous, as they both reduce the ionic concentration of the precipitate and do not appreciably solubilize the precipitate. In a particular embodiment, an aqueous polyethylene glycol (PEG) solution is employed as a wash buffer. Preferably the PEG has a molecular weight between about 0.25 to 50 kD (e.g., about 3 to 10 kD). The concentration of the PEG solution is preferably up to about 35% weight/volume (w/v) (e.g., about 5%, 10% or 15% w/v). The PEG concentration preferably is between about 5% and about 35% (w/v), more preferably between about 10% and about 35% (w/v). Any form of PEG can be employed including, without limitation, linear, branched or multi-arm PEGS, as well as derivatives and conjugates thereof. The precise concentration and molecular weight of PEG solution required to wash the protein precipitate can be determined empirically using the methods exemplified herein. Any art recognized means of washing the precipitate can be used including, without limitation, centrifugation in wash buffer.

Redissolving and Further Purification of the Protein

Following the separation of the protein (e.g., antibody) precipitate from the mixture, the precipitate can be redissolved in a buffer to form a protein solution. As shown herein, the use of citrate as a precipitant is particularly advantageous in that the resultant protein precipitate is readily soluble in small volumes (about 4 fold less than the volume of the original mixture) of buffer. Moreover, as shown herein, at least about 80% of the protein is typically recovered from the initial mixture.

The redissolution buffer can be any suitable buffer and will depend, at least in part, on the properties of the protein being isolated and whether the protein will be subject to any purification by chromatography. Preferably, the dissolution buffer has a pH of between 4.0 and 9.0. In a particular embodiment, the redissolution buffer comprises 50 mM citric acid and has a pH of about 4.8 and a conductivity of about 8 mS/cm. In another particular embodiment, the protein solution has a pH of lass than 7 and a conductivity of less than 20 mS/cm.

When used in conjunction with a downstream a chromatographic step, citrate precipitation can be used to reduce the volume of protein-containing material that needs to be applied to the chromatography column, and hence save on processing time. Any suitable art recognized chromatography technique can be employed to further purify the protein including, without limitation, ion-exchange, HIC or mixed mode chromatography. Suitable chromatography methods are described, for example, in WO06/110277, the entire contents of which are hereby incorporated by reference herein. For ion-exchange chromatography, the conductivity of the antibody solution is preferably less than about 20 mS/cm and the pH is preferably less than 7. This low conductivity is achieved, in part, by the washing step described above and the pH is dictated by the choice of resuspension buffer.

The present disclosure is further illustrated by the following examples, which should not be construed as further limiting. The contents of all figures and all references, patents and published patent applications cited throughout this application are expressly incorporated herein by reference in their entireties.

EXAMPLE 1

Comparison of Antibody Precipitation with Sodium Citrate or PEG

The following study demonstrates the superior performance of citrate over PEG as an antibody precipitant for antibody purification (e.g., large-scale purification). The following assay is easy, simple and quick to perform at small scales to optimize precipitation for different antibody molecules or upstream processes. Maximum precipitation concentration can be derived by tittering with different concentrations of sodium citrate in Eppendorf tubes and centrifuging the pellet and determining the leftover antibody level in the supernatant.

Figure 1A:
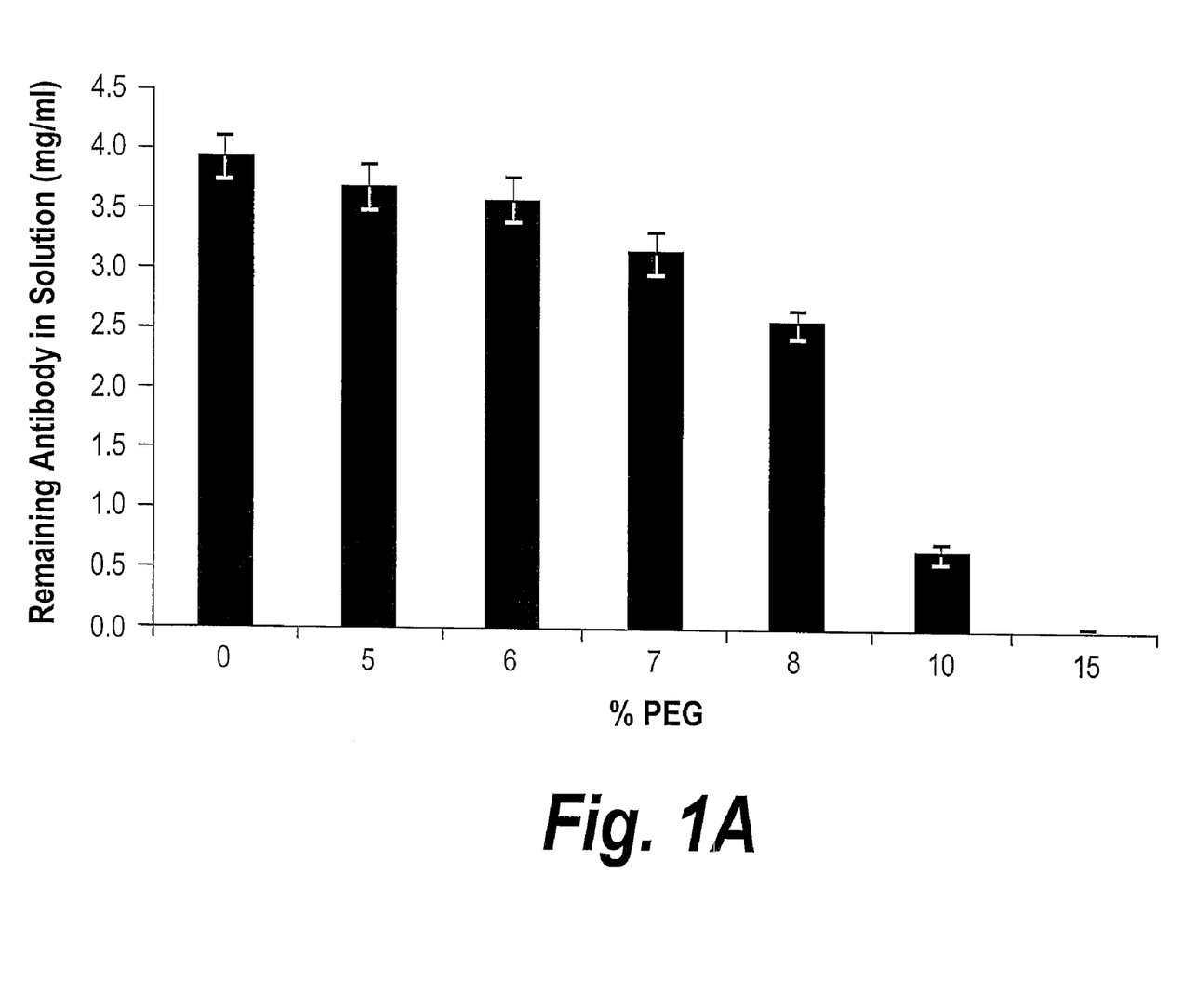
FIGS. 1A and 1B shows precipitation curves for the addition of sodium citrate (FIG. 1B) for four antibodies (A, B, C, D) including IGg1 and IGg4 isotypes, and PEG (FIG. 1A) for one antibody. Leftover antibody in solution was recovered after centrifugation and quantified by nephelometry for the sodium citrate addition and by Protein A HPLC for the addition of PEG. Error bars were defined to be 10% of the reading obtained.
Figure 1B:
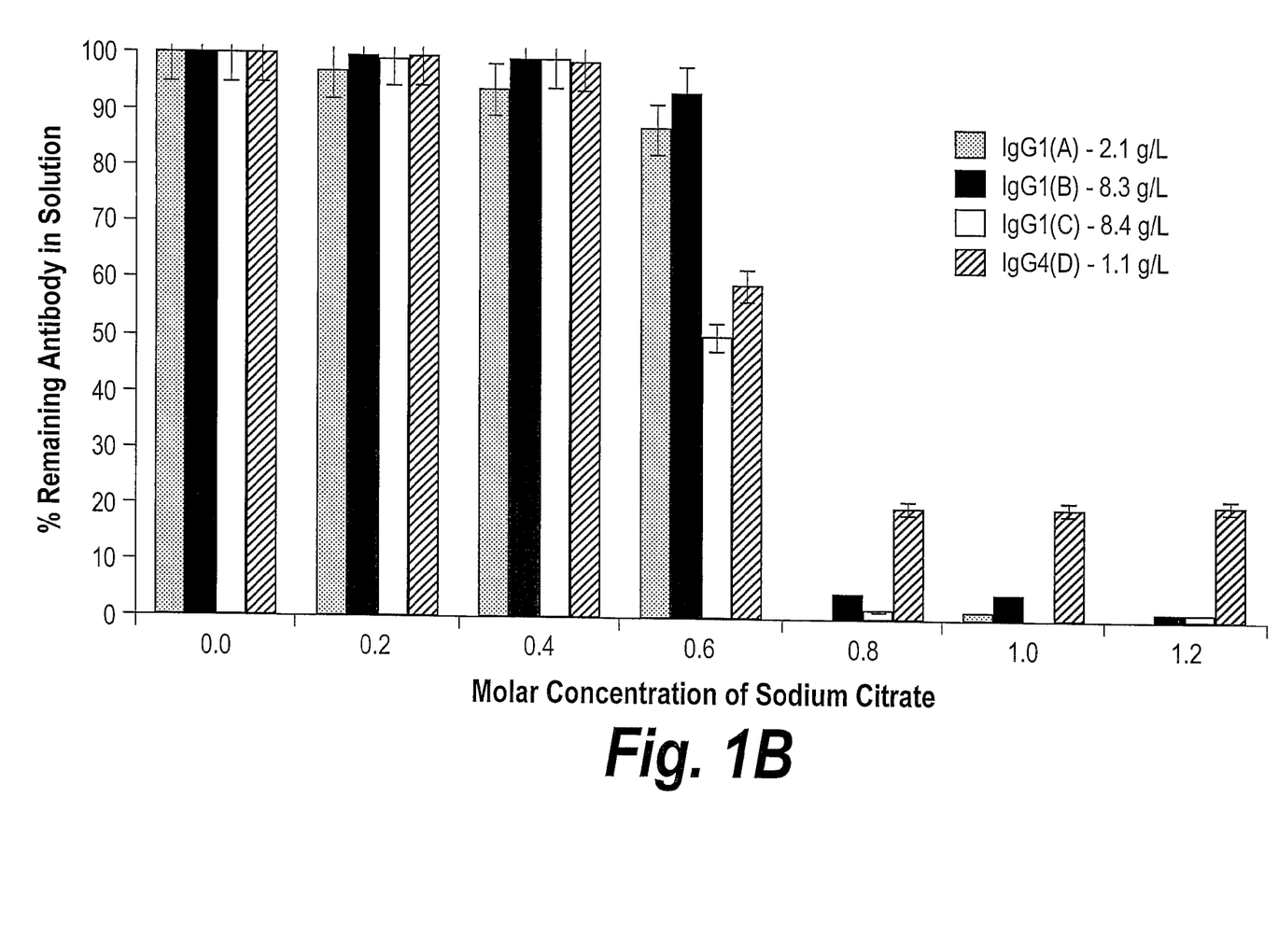

Different amounts of sodium citrate or PEG were added to a series of tubes containing antibody-containing, clarified cell culture media to precipitate the antibody. The remaining antibody in the supernatant after centrifugation was quantified by protein A HPLC. Representative precipitation curves are depicted in FIG. 1 and show that 0.8-1 M sodium citrate or 15% (w/v) PEG concentration are required for maximal antibody precipitation of the antibodies tested.

The pellet formed by the addition of sodium citrate was well compacted after centrifugation, and its resuspension in buffer occurred within minutes. Indeed, resuspension with a yield of over 80% was possible in as little volume as ¼ of the initial clarified cell culture media. In contrast, the precipitate formed by the addition of PEG alone was extremely compact, and its resuspension was more difficult, requiring vigorous agitation for a long time (typically over 45 minutes) and a larger volume (e.g., one third of the original clarified cell culture) of resuspension buffer for antibody recovery.

Figure 2:
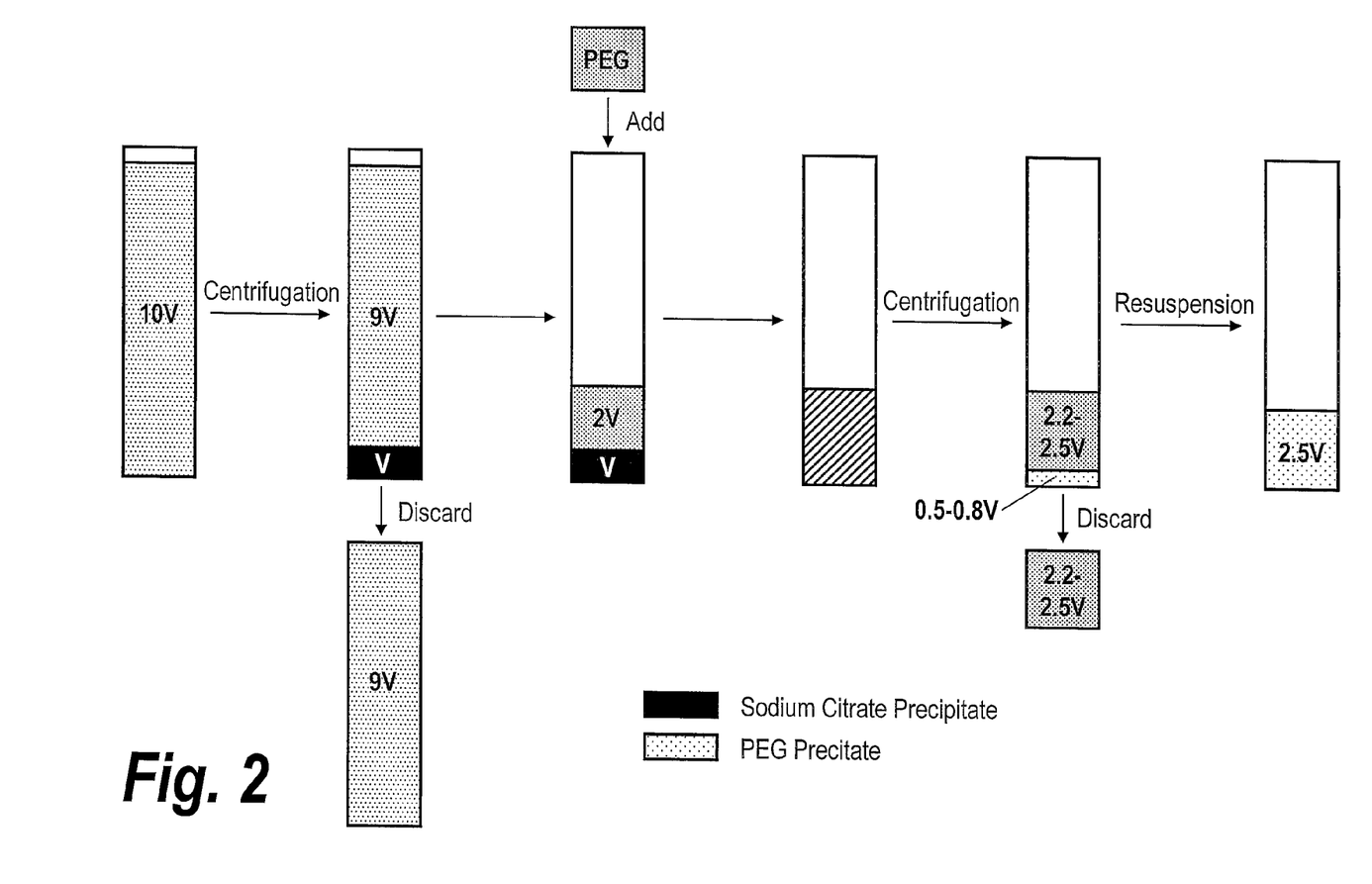
FIG. 2 provides a schematic of the citrate precipitation method, showing the relative processing volume (V) at each step. The PEG wash buffer is prepared such that during the wash step, the PEG concentration in the 2V volume units is >15% (w/v). The appropriate PEG concentration for the wash buffer is determined using a precipitation curve as in FIG. 1.

The presence of entrapped sodium citrate imposes high conductivity (approximately 35 mS/cm) and high pH (approximately pH 8) after the resuspension of the pellet. In order to reduce the ionic concentration (and hence the conductivity) of the solubilized pellet, the precipitate was washed with multiple compounds at saturation levels, whose solutions were characterized by negligible conductivity. However, only a PEG solution was capable of washing the precipitate without significant loss after resolubilization of the pellet. The precipitation curve shown in FIG. 1 was used to indicate the appropriate PEG concentration (15% w/v) to be used during the wash step. Since the citrate pellet had significant volume (about 10% the initial cell culture supernatant), the precipitate was washed with a more concentrated solution such that the final overall volume would correspond to the concentration of 15% (FIG. 2). This procedure not only allowed to condition the antibody in an appropriate matrix for binding onto an ion exchange resin, but the pellet was still easily solubilized after the PEG wash step.

In parallel, several resuspension buffer components were attempted to yield a processed material whose pH and conductivity were 4.5-4.8 and less than 15 mS/cm, respectively. These ranges allowed for effective binding of antibody on the cation exchange capture column. The final solution was found to be of 50 mM citric acid, yielding a pH of 4.8 and a conductivity of 8 mS/cm, approximately. The recovery with this procedure was found to be in the range of 85-95%.

In all cases, the biological activity of the antibody after precipitation, centrifugation and resuspension was checked by an ELISA assay. Neither sodium citrate nor PEG, at maximum precipitating concentrations, affected antibody activity when compared with a reference standard material generated from a three column purification process.

EXAMPLE 2

Figure 3:
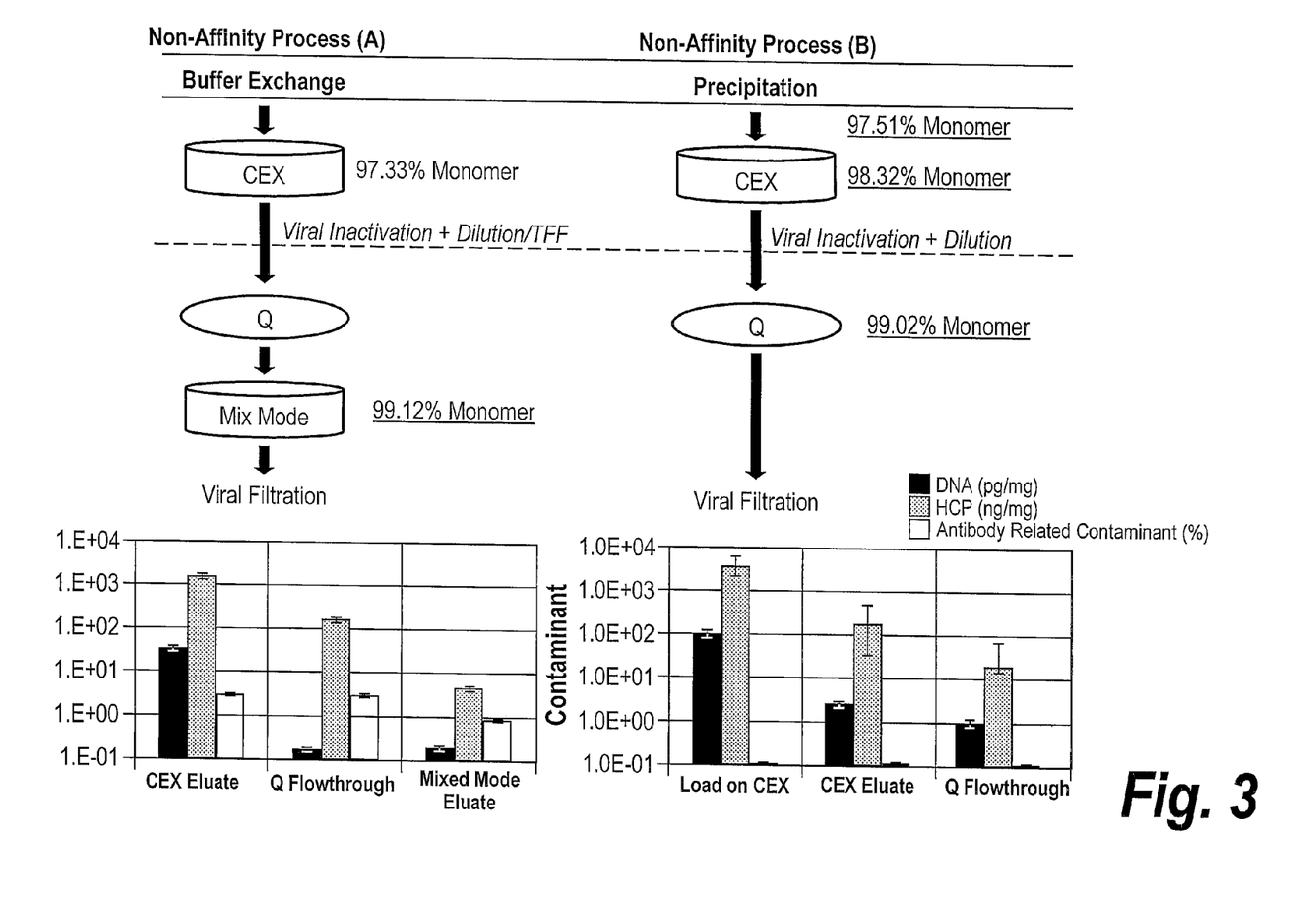
FIG. 3 provides a schematic of antibody purification by non-affinity Process A and non-affinity Process B, along with the HPLC-SEC purity levels (%) for the material produced at each step: cation exchange, Q and mixed mode steps for Process A and post-precipitation material, cation exchange and Q membrane steps for Process B. The dashed line represents the desired level of HCP and DNA content in the final purified material. Error bars are 20% for DNA and HCP, and the upper and lower limits measured for the antibody derived contaminant. For process B, low molecular weight, antibody-derived contaminants are removed by the citrate precipitation step prior to CEX chromatography.

Comparison of Antibody Purification Using Sodium Citrate Precipitation with Other Non-Affinity Antibody Purification Schemes The following study compared the results of two non-affinity antibody purification schemes. As illustrated in FIG. 3, Process A was a non-affinity process comprising three separation steps (without accounting for any chromatography cycles) and Process B was a two step non-affinity process using the citrate precipitation method for cell culture conditioning.

Process A started with an initial buffer exchange of the clarified cell culture supernatant to prepare the antibody into a matrix suitable for capture onto the cation exchange resin (CEX), followed by a dilution or in-process TFF preparing the antibody in another matrix, suitable to be processed by an anion membrane chromatography in a flow-through mode of operation, and finally a polishing of the material by a mixed mode resin. The capture cleared most of the DNA, endotoxin and host cell protein (HCP) of the load. The membrane chromatography cleared the residual amounts of these contaminants. A specific antibody associated contaminant was found to be co-purified along with the antibody. Western-blot analysis showed that the contaminant a light chain derivative. The existence of this contaminant imposes the need for an additional mixed mode column.

Process B started with an initial precipitation step by the addition of sodium citrate in a powder form. This precipitate was recovered by centrifugation and was subsequently washed with a PEG solution. A buffer then resolubilizes the precipitate to a final pH and conductivity values within the required range suitable for direct binding onto the cation exchange resin. The eluate contained residual HCP that was easily cleared by an anion exchange membrane to below detectable limits, though a dilution of the material to low conductivity values (<3 mS/cm) was required. However, considering the fast processing times for this unit operation, the volume was not a limiting factor.

For both purification schemes the starting material was an IgG1 antibody, produced using a CHO expression system in a fed-batch mode of operation. The final titer was 3.5±0.5 g/L. Cells were clarified by depth filtration. Both purification schemes were designed to yield product that was over 95% monomer, host cell protein less than 100 ng/mg and DNA less than 100 pg/mg. Product related contaminants were targeted to be below 1% of relative protein concentration (by absorbance at 280 nm). The reference quality level for the final purified product was determined by a three-step separation process, including three chromatography steps and having a Tangential flow filtration (TFF) as a conditioning step prior to capture.

The quality of the final purified material for Processes A and B was compared for host cell protein, DNA and antibody related contaminant content. The quantification of the antibody derived contaminant was estimated based on HPLC-SEC. FIG. 3 shows the differences in the measurements for these contaminants. DNA clearance was comparable. A striking result was observed at the end of the cation exchange process step: the host cell protein was at least 10-fold less for the non-affinity Process B relative to Process A. Variations were seen in the HCP content of the cation exchange eluate due to different scales and elution protocols. However, differences in HCP levels were efficiently cleared by the polishing Q step. This result suggests a significant difference in the population of HCP that is caused by the different processing methods of the clarified cell culture media. Also, it suggests that the nature of contaminants for the cation exchange for Process B is very different than those for Process A. The final established protocol for Process B resulted in an elution with less than 200 ng/mg antibody.

A striking and very pertinent result was found with the clearance of the small antibody derived contaminant. In Process A, it was difficult to separate this contaminant from the antibody and this specific contaminant was present in the cation exchange resin eluate, not removed by the Q polishing step. An additional column containing a mixed mode resin was accordingly needed to guarantee a robust clearance of this contaminant. In Process B, however, this contaminant was not even part of the precipitate, detected by HPLC-SEC, possibly related to the smaller molecular size and the less degree of hydrophobicity. Therefore, the mixed-mode resin column was not necessary. In other words, the three step purification scheme can be converted into a two step process scheme by using Process B. With the advent of ion membranes that claim the capability of antibody binding, the purification platform suggested by Process B offers the potential of having a fully membrane based scheme. Even in case of slightly lower binding capacity values, the fast processing flow rates will still be economically advantageous.

Table 1 summarizes estimated overall recovery and buffer usage for a process scaled-up to a 5000 L Bioreactor, 5 g/L titer and 100 L size columns. Binding capacity values were 85 mg/mL, and 25 mg/mL for the cation exchange and mixed-mode resins and loading capacity of 1000 mg/mL for Q membrane chromatography step, respectively. The largest size for the membrane chromatography was considered. The advantage of non-affinity Process B over non-affinity Process A is evident: about 50% of the usage of buffer, faster processing time, and a 2-fold higher productivity level (amount of antibody that can be processed per day) for equivalent purity and recovery.

TABLE 1

| | Non-Affinity Procee A | Non-Affinity Process B |
|---|---|---|
| Primary Recovery Yield (%) | ~95 | N/A |
| Precipitation Yield (%) | N/A | ~90 |
| CEX Chromatography Yield (%)/BC (mg/mL) | ~92/85 | ~90/85 |
| Q Chromatography Yield (%)/BC (mg/mL) | ~95/1000 | ~95/1000 |
| TFF Yield (%) | ~95 | N/A |
| MM Chromatography Yield (%)/BC (mg/mL) | ~100/25 | N/A |
| Overall Buffer Usage (L) | 44,111 | 16,961 |
| Final Purity (%) | 99 | 99 |
| Antibody Associated Contaminant ((%) | ~0.88 | <0.20 |
| Amount of Antibody Produced (g) | 19,927 | 19,575 |

The data in Table 1 presents the estimated process requirements for an antibody production process having a titer of 5 g/L and a 2000 L bioreactor. The following abbreviations are used in the table: CEX=cation exchange resin; Q=anion exchange membrane; MM=mixed mode resin; N/A=not applicable; BC=binding capacity.

Despite the different processes, viral clearance is provided by the same steps: a viral inactivation by low pH immediately after antibody capture, a viral filtration and the anionic membrane chromatography. The use of this technology is particularly advantageous in case of Process B since there is a dilution post-cation exchange step and processing volume is not a limiting factor for this technology. Depending on the antibody, if the host cell protein is cleared at the CEX level, Process B can be defined by a single precipitation step and a single chromatography column as long as the elution from the cation exchage resin takes place at a pH equal or lower than 5 and a Na+ concentration of less than 350 mM (Moscariello, 2008), therefore replacing the function of the membrane chromatography.

REFERENCES

The following references describe chromatography techniques suitable for use with the methods of the invention, and are hereby incorporated by reference in their entirety:

Ahamed, T., et al. (2007) Selection of pH-related parameters in ion-exchange chromatography using pH-gradient operations. Journal of Chromatography A., 1194(1):22-29. Available online Dec. 8, 2007.

Arunakumari, A., Wang J. and G. Ferreira. (2007). Alternatives to Protein A: Improved Downstream Process Design for Human Monoclonal Antibody Production. Biopharm International, Feb. 2, 2007.

Foster P. R., Dunnill, P. and M. D. Lilly. (2004). "The kinetics of protein salting-out: precipitation of yeast enzymes by ammonium sulfate". Biotechnology and Bioengineering, 18(4): 545-580.

Gagnon, P. (1996) "Purification Tools for Monoclonal Antibodies". Validated Biosystems, Tucson, Ariz. (ISBN: 0-9653515-9-9).

Gagnon, P. (2000). "Use of Hydrophobic Interaction Chromatography with a Non-Salt Buffer System for Improving Process Economics in Purification of Monoclonal Antibodies". Waterside Conference on Monoclonal and Recombinant Antibodies, Miami Fla., Tosoh.

Matheus, S., Friess, W., Schwartz, D. And Mahler H C. (2008). "Liquid high concentration IgG1 antibody formulations by precipitation". Journal of Pharmaceutical Sciences (Epub ahead of print).

Moscariello, J. (2008). "Comparison of Potential Monoclonal Antibody Purification Processes with Two Chromatography Steps". BioProcess International Conference, Anaheim, Calif.

Shields, Chris. (2008). "Advances in Single Use Capture Chromatography". BioProcess International Conference, Anaheim, Calif.

Ramanan, S. and Stenson, R. (2008). Method of Isolating Antibodies by Precipitation. WO 2008/100578 A2.

Vilmorin, P. (2008). "Scale-up evaluation of selective antibody precipitation and continuous recovery with a disc-stack centrifuge". BioProcess International Conference, Anaheim, Calif.

Wang, J. Diehl, T., Watkins-Fischl, M., Perkins, D., Aguiar, D., and A. Arunakumari. (2008). "Optimizing the primary recovery step in nonaffinity purification schemes for HuMAbs". BioPharm International, Mar. 2, 2008.

Zellner, et al. "Quantitative validation of different protein precipitation methods in proteome analysis of blood platelets". Electrophoresis, 2005 Jun.; 26(12):2481-9.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

What is claimed is:

1. A method of obtaining a protein in purified form from a mixture comprising the protein and one or more contaminants, comprising:
   (a) adding citrate to the mixture to form a precipitate of the protein, wherein the mixture comprises contaminants from the production of the protein using a host cell culture;
   (b) separating the precipitate of the protein from the mixture;
   (c) dissolving the precipitate of the protein in a solvent to form a solution of the protein; and
   (d) subjecting the solution to ion exchange chromatography, hydrophobic interaction chromatography, affinity chromatography, mimetic chromatography, or mixed mode chromatography, to further purify the protein.

2. A method according to claim 1, wherein the protein is an antibody.

3. A method according to claim 1, wherein a co-precipitant is added with the citrate.

4. A method according to claim 1, further comprising the step of reducing the ionic concentration of the protein by contacting the precipitate of the protein with a wash buffer.

5. A method according to claim 4, wherein the wash buffer comprises a polyether.

6. A method according to claim 5, wherein the polyether is PEG.

7. A method of obtaining a protein in purified form from a mixture comprising the protein and one or more contaminants, comprising:
   (a) adding citrate to the mixture to form a precipitate of the protein;
   (b) separating the precipitate of the protein from the mixture; and
   (c) reducing the ionic concentration of the protein by contacting the precipitate of the protein with a wash buffer.

8. A method according to claim 7, wherein the wash buffer comprises a polyether.

9. A method according to claim 8, wherein the polyether is PEG.

10. A method according to claim 7, further comprising:
    (a) dissolving the precipitate of the protein in a solvent to form a solution of the protein; and
    (b) subjecting the solution to ion exchange chromatography, hydrophobic interaction chromatography, affinity chromatography, mimetic chromatography, or mixed mode chromatography, to further purify the protein.

11. A method according to claim 10, wherein the protein is an antibody.

12. A method according to claim 7, wherein the protein is an antibody.

13. A method according to claim 7, wherein the mixture comprises contaminants from the production of the protein using a host cell culture.

* * * * *